(12) United States Patent
Chesner et al.

(10) Patent No.: US 8,902,422 B2
(45) Date of Patent: Dec. 2, 2014

(54) BULK MATERIAL SAMPLING AND LASER TARGETING SYSTEM

(71) Applicant: Chesner Engineering. P.C., Long Beach, NY (US)

(72) Inventors: Warren H. Chesner, Oceanside, NY (US); Matteo Forgione, Templeton, MA (US); Henry G Justus, Union, CT (US)

(73) Assignee: Chesner Engineering, PC, Long Beach, NY (US)

( * ) Notice: Subject to any disclaimer, the term of this patent is extended or adjusted under 35 U.S.C. 154(b) by 283 days.

(21) Appl. No.: 13/653,017

(22) Filed: Oct. 16, 2012

(65) Prior Publication Data

US 2013/0100444 A1    Apr. 25, 2013

Related U.S. Application Data

(60) Provisional application No. 61/628,015, filed on Oct. 21, 2011.

(51) Int. Cl.
| | | |
|---|---|---|
| *G01J 3/30* | (2006.01) | |
| *G01J 3/443* | (2006.01) | |
| *G01N 21/71* | (2006.01) | |
| *G01N 21/85* | (2006.01) | |

(52) U.S. Cl.
CPC ............... *G01J 3/443* (2013.01); *G01N 21/718* (2013.01); *G01N 21/85* (2013.01); *G01N 2021/8592* (2013.01)
USPC ........................................................ 356/318

(58) Field of Classification Search
CPC ............... G01N 21/718; G01N 21/645; G01N 21/6458; G01J 3/4406; G01J 3/02
USPC ........................................................ 356/318
See application file for complete search history.

(56) References Cited

U.S. PATENT DOCUMENTS

| | | | |
|---|---|---|---|
| 4,428,902 A | 1/1984 | Murray | |
| 4,582,992 A | 4/1986 | Atwell et al. | |
| 5,818,899 A | 10/1998 | Connolly et al. | |
| 6,438,189 B1 | 8/2002 | Vourvopoulos | |
| 7,006,919 B2 | 2/2006 | Osucha et al. | |
| 2002/0149768 A1* | 10/2002 | Sabsabi et al. | 356/318 |
| 2003/0197125 A1* | 10/2003 | De Saro et al. | 250/339.07 |
| 2003/0225531 A1 | 12/2003 | Lingren et al. | |
| 2003/0231304 A1* | 12/2003 | Chan et al. | 356/301 |
| 2004/0183018 A1* | 9/2004 | Zhou et al. | 250/341.1 |
| 2007/0263212 A1 | 11/2007 | Mound | |
| 2009/0073586 A1* | 3/2009 | Fry et al. | 359/839 |
| 2009/0091745 A1* | 4/2009 | Levesque et al. | 356/73 |

OTHER PUBLICATIONS

Cremers Handbook of Laser Induced BS forward, 2006, 5 pages.
Misiolek, et al Laser Induced Breakdown Spectroscopy, 2006, 10 pages.
Gaft Laser Induced Spectra Bulk, 2007, 8 pages.
Singh, et al Laser Induced Breakdown Spectroscopy, 14 pages, 2008.
Noll Laser Induced Breakdown Spectroscopy, 7 pages, 2011.

* cited by examiner

*Primary Examiner* — Tarifur Chowdhury
*Assistant Examiner* — MD Rahman
(74) *Attorney, Agent, or Firm* — Alfred M. Walker

(57) ABSTRACT

A method is described for providing a continuous flow of a target material past a laser to enable repeated firings of the laser beam at the material in a controlled and uniform fashion. The objective is to provide a means to characterize the target material using laser induced breakdown spectroscopy. The method can be employed in a laboratory or field environment providing improved methods for characterizing in real time the properties of bulk materials.

17 Claims, 4 Drawing Sheets

BULK MATERIAL SAMPLING AND LASER TARGETING SYSTEM

RELATED APPLICATIONS

This application is based upon Provisional Application No. 61/628,015, filed Oct. 21, 2011, which application is incorporated by reference herein. Applicant claims priority under 35 U.S.C. 119 (e) therefrom.

FIELD OF THE INVENTION

The present invention relates to a bulk sampling and laser-targeting system (SLT) that provides for continuous or semi-continuous monitoring of a bulk stream of material.

BACKGROUND OF THE INVENTION

Laser induced breakdown spectroscopy (LIBS) is a technology that is based on a process called laser ablation. The basic idea of laser ablation is relatively straightforward. A high powered pulsed laser, capable of achieving a very high irradiance, is focused, using a system of mirrors and lenses onto a very tiny spot on a target material. When the laser energy exceeds the ablation threshold energy of the material, chemical bonds are broken and the material is fractured into energetic fragments. These fragments include a mixture of neutral atoms, molecules and ions inducing plasma. During plasma formation, electrons interact and subsequently, within microseconds, recombine with ions to release energy across a broad spectral range, most importantly for LIBS between 200 to 980 nanometers. Basic LIBS equipment, which are commercially available include a pulsed laser, capable of inducing sufficient irradiance to ablate a sample target, a light collection system, consisting of lenses mirrors or a fiber optic that collects the plasma light and transports the light to a detection system, a detection system, such as spectrograph and a detector, such as a charged couple detector, to record the light and computer and electronics to gate the detector, fire the laser and store the spectra.

The light generated by the plasma is characteristic of the chemical makeup of the ablated material. This light (emission) can be quantified by collecting it and generating a spectral image that identifies the emission wavelengths and respective intensities in a spectrometer. This spectral image can be visually and mathematically recorded in a computer. Once stored it is possible to make use of spectral patterns to quantify elemental concentrations present in the sample. For example, each element emits a characteristic set of discrete wavelengths according to its electronic structure. By observing these wavelengths and their respective emission intensities, the elemental composition of the sample can be determined. As such, LIBS is fundamentally similar to other traditional atomic emission spectroscopic methods; but unlike traditional methods lasers have the unique advantage of providing real-time "remote sensing" capability both in the laboratory and in particular in field applications, without special sample preparation.

During the past decade, the dissemination of information and descriptions of potential applications for this technology has appeared in numerous publications such as the Journal of Applied Spectroscopy, the Journal of Analytical Atomic Spectrometry, and the Journal of Applied Optics and Spectrochimica Acta. In addition, the topic has generated the publication of no less than four textbooks devoted to the subject, including Noll, R., Laser Induced Breakdown Spectroscopy, Springer-Verlag, Berlin Heidelberg 2012, Cremers, D. and L. J. Radziemski, Handbook of Laser-Induced Breakdown Spectroscopy, John Wiley, England 2006, Singh, J. P. and S. N. Thakur, Laser-Induced Breakdown Spectroscopy, Elsevier, Amsterdam 2007, and Mizolek, A. W and V. Palleschi and I. Schecter, Laser-Induced Breakdown Spectroscopy, Cambridge University Press, New York, 2006. These texts describe not only the fundamentals of the technology, but numerous potential applications for which the LIBS technology can be employed. Some of these applications include archaeological material analysis, toxic materials identification in liquids, explosive material detection, soil analysis, food contamination, geologic material and gemstone identification, and metal alloy detection. The National Aeronautics and Space Administration (NASA) is employing LIBS technology in space on the exploration vehicle, Curiosity that touched down on the Mars landscape on Aug. 13, 2012, to determine the mineralogy of soil and rock on the Martian landscape.

Despite the number of potential applications and its current use in space, LIBS technology has been slow to be deployed in bulk material commercial applications. Most of the current LIBS applications employ techniques that focus on precise targeting at a fixed focal point. Each time a new target is identified a new focal point is established and the laser is fired sometimes at 1-50 Hz to collect spectral information about the target. These systems are referred to herein as "shot to shot" systems. The goal of such systems is try to duplicate, to the extent possible, the conditions each and every time the laser fires at the sample target. In shot to shot systems, the sample population is relatively low and since only a very small area (typically less than 0.2 mm in diameter) is targeted, it is critical in such systems that the selected target location be representative of the sample. It is also important that the laser and optical collection and detection system operate at highly stable conditions to eliminate fluctuations in the spectral output. Shot to shot system stability is extremely important for LIBS because any change in operating parameters such as laser power, focal length, system temperature or environmental conditions could alter the properties of the plasma matrix and the resulting spectral output; and with few samples the spectral output could clearly misrepresent the target material. Such systems are most effective when the target material has a high degree of homogeneity from sample to sample.

In many industrial applications it is desirable to provide in-line, real time continuous or semi-continuous monitoring of bulk materials that display a significant degree of heterogeneity during the production process. The purpose is to provide improved quality control procedures. This requires monitoring systems that can continuously scan high volumes of materials, and data processing systems that incorporate analytical techniques that can integrate the data, in this case the spectral outputs, into information about the nature of the target material. Examples of industrial applications where the monitoring systems would be of great utility include the Portland and asphalt concrete production industries, and the cement, glass, steel, coal, mining and mineral aggregate production industries.

A current method for in-line bulk materials analysis, particularly in the cement, coal and mining industry is prompt gamma ray neutron activation analysis (PGNAA). In this technology the bulk material is bombarded with neutrons as it passes a neutron source, releasing gamma rays. Different gamma ray energy spectra are produced from different elements in the bulk materials. By processing these detected signals, the elements present in the bulk sample can be quantified. Similar systems are being researched and deployed using x-ray fluorescence (XRF), PGNAA and XRF are further advanced than LIBS in their commercial deployment. Up until now, with the few exceptions outlined below, LIBS systems have not been used in bulk sampling in an industrial environment. This is because the heterogeneity of samples with respect to chemical properties, moisture content, dust particles and atmospheric conditions, such as humidity and temperature as well as gas composition interferes with the laser irradiation and spectra generated by the laser shot. In addition, rapid firing of a laser at a moving stream of bulk material will not always result in a constant laser to target focal length, introducing additional variation in the spectral output. The subject invention is designed to transform the use of LIBS from a "shot to shot" laboratory or a roving mobile system to an industrial monitoring system capable of providing quality control monitoring of bulk materials. Bulk materials used in the context of this invention are coarse granular materials or fine grained granular material or powdered materials. Examples of such materials include, mineral aggregates used in construction, mined ores, geologic rock, glass, cement, and coal. Such materials can be chemically heterogeneous, depending on the source, and tend to be processed in large quantities on the order of tons per hour. Determining the chemical, physical and mechanical nature of such materials, in real time, is difficult without the use of a continuous in-line monitoring system that can collect and process large quantities of spectral data to provide information on the nature of the material. Such information can be used as a quality control tool to reject or accept materials during processing.

There are at least four common features in bulk monitoring emission spectroscopic detection systems, regardless of the technology employed. The first is that a source of energy must be available to target the bulk materials. The second is that the bulk material or subsamples of the bulk materials must be transported to or passed near the source to expose the bulk material to the energy source. The third is that the atomic emission released from the targeted material must be captured in a suitable detector and the fourth is that the information detected must be processed and translated into quantifiable information that is suitable for the quality control objectives. To integrate all four features into an operating system, a suitable material transport and targeting and environmental control system must be available to practically adapt the process to the specific technology (PGNAA, XRF, or LIBS) being employed.

The following summaries of prior art focus on the integrated process strategies that have been reported for PGNAA, XRF and LIBS systems:

Atwell (U.S. Pat. No. 4,582,992) describes a real time PGNAA bulk material analyzer in a self-contained sealed air conditioned housing, where bulk material is channeled through a vertical three foot chute. Atwell describes chute deployment at the end of a conveyor belt and the transport of material vertically down through the chute to a lower conveyor. The radiation sources and the detectors are symmetrically located on opposite sides of the chute to target the materials with neutrons and detect the gamma ray emissions. Such systems must be extremely well sealed to prevent any release of gamma radiation. Vourvopoulos (U.S. Pat. No. 6,438,189 B1) describes a system in which the inventor introduces an apparatus, which appears to be a bifurcated hopper that is used to direct a portion of a target material (particularly coal or cement) from the main chute to an alternative or secondary chute. The main chute is surrounded by a neutron generator and a system of gamma ray and neutron detectors. The alternative chute receives gamma emissions resulting from reactions in the main chute, and generates secondary emissions that are also recorded. The combination the main and secondary spectral outputs are analyzed to yield the elemental composition of the target material. Lingren (US Patent 2003/0225531 A1) describes the use of a PGNAA source and gamma ray detectors integrated into a specially designed cylindrical housing with an inner and outer chamber to protect the release of radiation. Osucha (U.S. Pat. No. 7,006,919 B2) describes another similar method of irradiating a flowing material on a conveyor with neutrons as part of a PGNAA detection process, but Osucha's emphasis is the development of a library of spectra to match the spectral output of unknown samples with unknown levels of impurities to the spectra of samples with known levels of impurities. The objective is to predict the level of impurities in the unknown samples.

Murray (U.S. Pat. No. 4,428,902) describes a system in which high energy x-rays from an electron accelerator induce the emission of gamma rays from a target material, specifically coal, to measure the oxygen and sulfur content of the targeted coal samples. In Murray's embodiment, the x-rays from a linear accelerator are directed from a location above the conveyor belt carrying the coal, irradiating the coal with a subsequent release of gamma rays. The gamma radiation is detected by a suitable gamma ray spectrometer located under the conveyor to determine the quality of the coal. Again, such systems must be extremely well shielded to protect exposure to dangerous gamma radiation.

Connolly (U.S. Pat. No. 5,818,899) describes a system in which an x-ray transmitter and an x-ray fluorescent detector are integrated into a pulverized coal (powder) supply line to determine the chemical composition of the coal. Connolly's invention provides for a recessed chamber within the coal feed line (tube) that is designed to collect discrete pulverized coal samples at predefined intervals. The samples are subsequently bombarded through a transparent window in the recessed chamber with x-rays. An adjacent probe receives fluorescence resulting from the x-ray bombardment and transmits the data for subsequent analysis. Pressurized air discharges the powdered coal back into the coal feed line after the analysis, providing room for the next sample to be collected. Mound (US Patent US 2007/0263212 A1) describes a non-hazardous bulk material analyzer system that makes use of white light (not x-rays or gamma radiation or laser light) to scan target materials (focusing on cement) from a source located above a conveyor. Mound also describes the use of pre-calibrated spectra that are generated using chemometric techniques to provide a stored library of spectra to which unknown samples can be compared. Mound does not describe the chemometric techniques and provides no specifications on specific sources of white light, emission detectors, nor does he address any of the myriad of interfering factors, such as dust or focal length control, or environmental control that would be needed to practically apply such a system in an industrial setting. Sommer (U.S. Pat. No. 7,616,733 B2) describes the use of an XRF system deployed on a conveyor belt that can be sequentially irradiated with x-rays, along the length of the belt to identify and, sort the target material, particularly ferrous and nonferrous materials from automobile shredding operations.

There are numerous patents that have been filed that focus on "shot to shot" (laboratory based in most cases) LIBS systems incorporating specific applications or equipment innovations or arrangements. It is much easier to control factors that define the plasma matrix in controlled shot to shot systems where the target is placed at a fixed focal point and where environmental conditions are better controlled than an industrial processing line. Integrating LIBS into an in-line processing system, requires a LIBS process that can sample and process the target in a way that manages the environmental factors and processes the data generated.

The first US Patent to express the use of LIBS system for monitoring bulk materials in an in-line process is believed to be Potzschke (U.S. Pat. No. 5,042,947). Potzschke describes a method for using a LIBS system on a conveyor belt to identify the composition of scrap metal, but provides little detail on the physical nature of such a system and how it would target the material. Graft (U.S. Pat. No. 6,753,957 B1) describes an in-line bulk monitoring LIBS system designed to target bulk materials, particularly phosphate rock being conveyed on a moving belt. To resolve spectral resolution problems, Graft focuses his invention on analytical techniques through the development of spectral elemental signature ratios to determine whether a specific element is present or not in the sample. In a subsequent publication (Gat M.; Sapir-Sofer, I.; Modiano, H.; Stana, R. Laser induced breakdown spectroscopy for bulk minerals online analyses, Spectrochimica Acta Part B: Atomic Spectroscopy, Volume 62, Issue 12, December 2007, p. 1496-1503) Gaft (Note: Gaft is believed to be the Graft of U.S. Pat. No. 6,753,957B1) reported on the development of a LIBS in-line conveyor and field prototype unit for phosphate rock ore analysis and the ash content evaluation of coal. He describes a LIBS system located over a conveyor belt carrying phosphate ores containing sealed panels, shock absorbers and air conditioning to enable outdoor operation.

Laser targeting of bulk materials is limited by the harsh, dust-laden and vibrating environments associated with industrial processing operations. Such environments can interfere with laser targeting and the laser to target focal length, which can alter poorly understood matrix effects associated with the ablation process. Non-uniform ablation conditions could significantly affect the intensities and spectral emission of the process. In addition, the presence of dust and the atmospheric gas composition, including the humidity, in the vicinity of the laser induced ablation, and moisture in the samples could interfere with the laser energy reaching the targeted material and the nature of plasma formation and ultimately the light emitted during the ablation process. The laser and optical system must be segregated from the dust particles to prevent a buildup of dust in the system and corresponding operational difficulties. Finally, safety issues in a bulk material production environment demands that eye or skin exposure to operating personnel be avoided. Open and exposed targeting of materials in such an environment would be problematic.

The subject invention is designed to transform the use of LIBS from a "shot to shot" laboratory or a roving mobile system to an industrial monitoring system capable of providing quality control monitoring of bulk materials. Bulk materials used in the context of this patent are high volume coarse granular materials or fine grained granular material or powdered materials LIBS spectra are well suited as input data for use in the development of chemometric multivariate statistical models. Multivariate statistical models are capable of quantifying patterns in the spectra data, which is generated by the laser ablation process. Such models are most effectively applied by establishing a spectral pattern model associated with a known sample, referred to as the calibration sample, and using this defined calibration model to discriminate and identify similar or dissimilar patterns in unknown samples. This technique of pattern matching is similar to fingerprinting. As part of the subject invention, as will become apparent, the inventor makes use of these models to assist in processing and interpreting an extremely large output of spectral data generated as a result of the sampling and targeting system discussed in this patent. It is this Sampling and Targeting System, referred to as the SLT, which provides the means to process bulk materials through a specially conceived laser-optics system designed to procure data necessary for characterizing the bulk materials.

OBJECTS OF THE INVENTION

The invention disclosed is intended as a means to provide a sampling and laser targeting system that can be used in laboratory or field environments to characterize bulk materials.

SUMMARY OF THE INVENTION

The invention described herein is a bulk sampling and laser-targeting system (SLT) that is designed to provide for continuous or semi-continuous monitoring of a bulk stream of material. The invention can be used as stand-alone or laboratory system where sample buckets are deposited into the system. It can be deployed adjacent to a moving conveyor line of bulk material, where a subsample of the target material is diverted into the SLT for analysis, or it can be employed in such a manner that the entire bulk stream is directed into and through the entire system.

In all cases the target material to be analyzed is directed into and through the SLT unit, described in greater detail below. This material diversion provides the means to minimize interferences that would be encountered in a direct in-line monitoring system, for example where the laser is directed at a process line conveyor belt, without diminishing the effectiveness of the laser monitoring system to obtain large quantities of data necessary to properly characterize the targeted material. The SLT system is enclosed in a separate sealed housing disconnected from the main bulk material conveying system, thereby ensuring a contained and safe operation. The subject invention also provides the means to address issues of sample heterogeneity, sample moisture content, interfering dust and temperature and humidity conditions, all of which could further compromise the quality of the spectral data.

As will become apparent upon review of the drawings and discussion of the drawings presented below, the invention includes a system that transports samples of bulk material through a material flow chute that serves as a laser targeting chamber designed with dimensions that are dependent on the size of the aggregate particles that comprise the target material. The system can practically process materials from powdered size, such as cement or fly ash to mineral aggregates used in construction operations to mined ores. The size of the target material is only limited by the size of the laser targeting chamber. In addition, the size and weight of the SLT system will in most instances be small enough to be used in a laboratory environment. So for example, batch subsamples of materials could be transported to a laboratory and analyzed in lieu of continuous or semi-continuous field monitoring systems.

Furthermore, while most inventors have focused on standard spectral data analytical techniques in which two variables (wavelength and intensity) or ratios of these variables, are correlated with elemental concentration, this invention employs additional data management techniques that are better suited for LIBS bulk in-line monitoring. More specifically the invention makes use of multivariate chemometric models using principal components analysis (PCA) and partial least squares (PLS) regression analysis. Those versed in the art of PCA and PLS will recognize that such chemometric modeling can be used to 1) explore patterns of association in data, 2) prepare and use multivariate classification or discriminant models, and 3) track properties of materials on a continuous basis. PLS discriminant analysis can be used to distinguish materials with similar or differing properties. Such properties can include the chemical, physical or mechanical properties of the target material. As such, spectral data generated can be used, not only to determine the chemical composition of the material, but engineering properties. Such properties can include for example, strength, reactivity and conductivity or any suitable property used to describe the nature of the material. This is achieved by generating spectral chemometric calibration models with materials that contain known properties, and comparing such models with spectral outputs of unknown samples.

In a bulk monitoring system, it is possible to collect large quantities of data, resulting from the continuous or semi-continuous operation. The sample population is extremely large compared to shot to shot systems. Generating a large database of spectra, averaging the spectral patterns, and incorporating average spectra into the chemometric model assist in accounting for expected errant spectral outputs. Incorporating errant spectral patterns into the model by averaging all spectra provides the means to account for system variations, such as focal length in particular, when developing the model. In addition, averaging large quantities of spectral data can also be used by the chemometric models to account for the heterogeneity of the samples, while targeting one specific property of interest. Such modeling has been shown to identify the physical and mechanical as well as the chemical properties of a target material. The inventors have provided such data in a recent report submitted to the National Academy of Sciences on this matter (Chesner W. H. and N McMillan, Automated Laser Spectrographic Pattern Matching for Aggregate Identification, Final Report for Highway IDEA Project 150, Transportation Research Board of the National Academies, Apr. 18, 2012).

BRIEF DESCRIPTION OF THE DRAWINGS

The present invention can best be understood in connection with the accompanying drawings. It is noted that the invention is not limited to the precise embodiments shown in drawings, in which.

LIST OF REFERENCE NUMERALS

1. Material Flow System
2. Laser-Optical System
3. Dust Suppression System
4. Source Target Material
5. Source Feed Hopper
6. Material Flow Chute
7. Migrating Material
8. Flow Control Disk
9. Exiting Material
10. Laser Target Orifice
11. Laser Beam
12. Quartz Window
13. Rotating Disk Rod
14. Mixing Tool
15. Blank
16. Laser
17. First Reflecting Mirror
18. Second Reflecting Mirror
19. Waveguide
20. Spectrometer and Charged Couple Detector
21. Computer
22. Emission Spectra
23. Dust Suppression Tube
24. Air Compressor
25. Air Heater and Blower
26. Variable Speed Motor

DESCRIPTION OF A PREFERRED EMBODIMENT OF THE INVENTION

The subject invention as described above is intended to serve as a Sampling and Laser Targeting System, or SLT System, which can be used in laboratory or field environment to characterize bulk materials.

Figure 1:
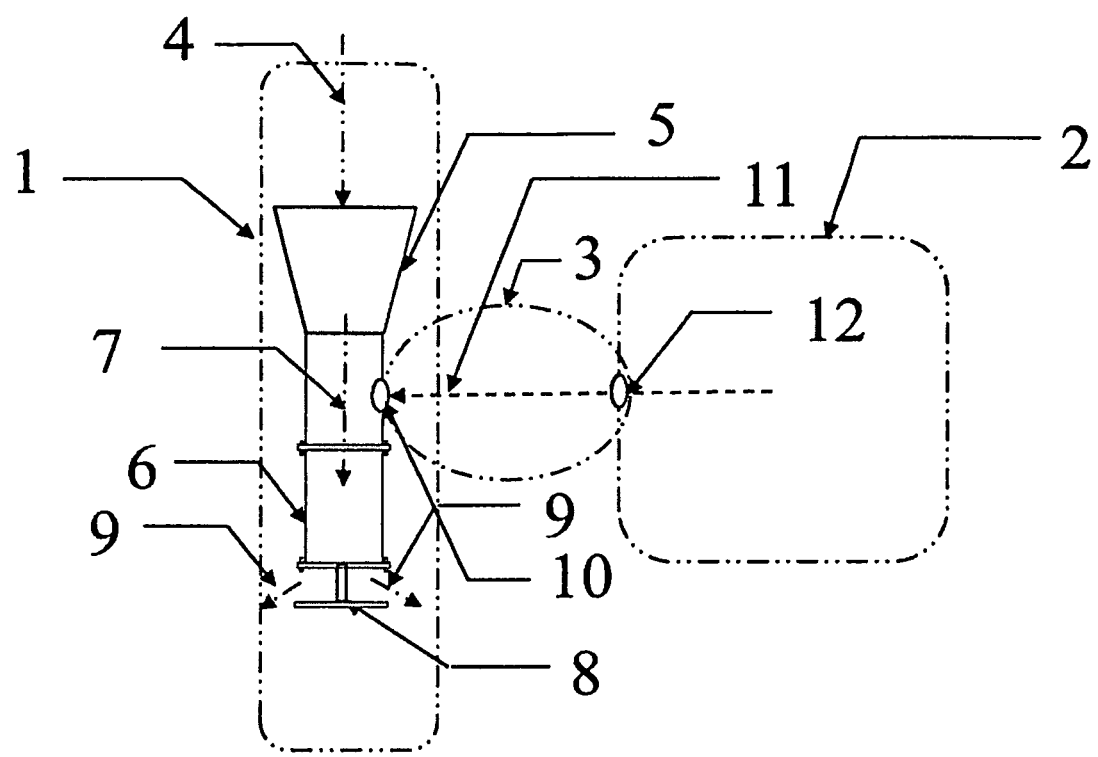
FIG. 1 provides a sectional view of the Sampling and Laser Targeting System (SLT), configured to provide for bulk material flow system that moves bulk material uniformly passed a targeting laser capable of ablating a tiny mass of targeted material, an optical system capable of transmitting and receiving light, and a dust suppression system capable of preventing dust from interfering with the process and also providing the means to reduce moisture present in the target material, if necessary.

Referring to the drawing, shown in FIG. 1 a side view of the SLT System is depicted. The SLT System consists of three primary components. These include a Materials Flow System 1, a Laser-Optics System 2, and a Dust Suppression System 3. Source Target Materials 4, which can include coarse grained solid granular materials, fine grained solid granular materials or even powder-like materials, can be diverted into the Material Flow System 1 by depositing the materials into the Source Feed Hopper 5.

The Source Target Materials 4 can be diverted off a conveyor system using automated commercially available conveyor sweeper systems, which can readily divert material moving along a conveyor belt into the Source Feed Hopper 5, or at other locations where moving materials may be readily diverted, such as conveyor drop-offs where diversion plates or bifurcated hoppers can redirect bulk material flow as needed into the Source Feed Hopper 5. If it is convenient to forego the use of automated material feed systems, the Source Target Materials 4 can be diverted by manual means. The volume of sample used is limited by the size of the hopper and the desired frequency of material sampling to be explained in greater detail below. It is envisioned that a typical sample volume entering the SLT at any one time will consist of one to 5 gallons. The size of the Source Target Materials 4, as measured by the particulate diameter, is limited by the diameter of the Material Flow Chute 6. The diameter of the Material Flow Chute 6 should preferably be greater than 5 to 6 times the largest particulate diameter of the Source Target Materials 4 to avoid clogging of the Materials Flow System 1. Additional features to prevent clogging of the Material Flow Chute 6 are described below. The Source Target Materials 4 are contained in the Material Flow Chute 6 by the presence of a Flow Control Disk 8, which is discussed in greater detail below. The Flow Control Disk 8 can be hydraulically or mechanically driven to open or close the bottom of the Material Flow Chute 6, by moving in an up (to close) or down (to open) direction.

Figure 2:
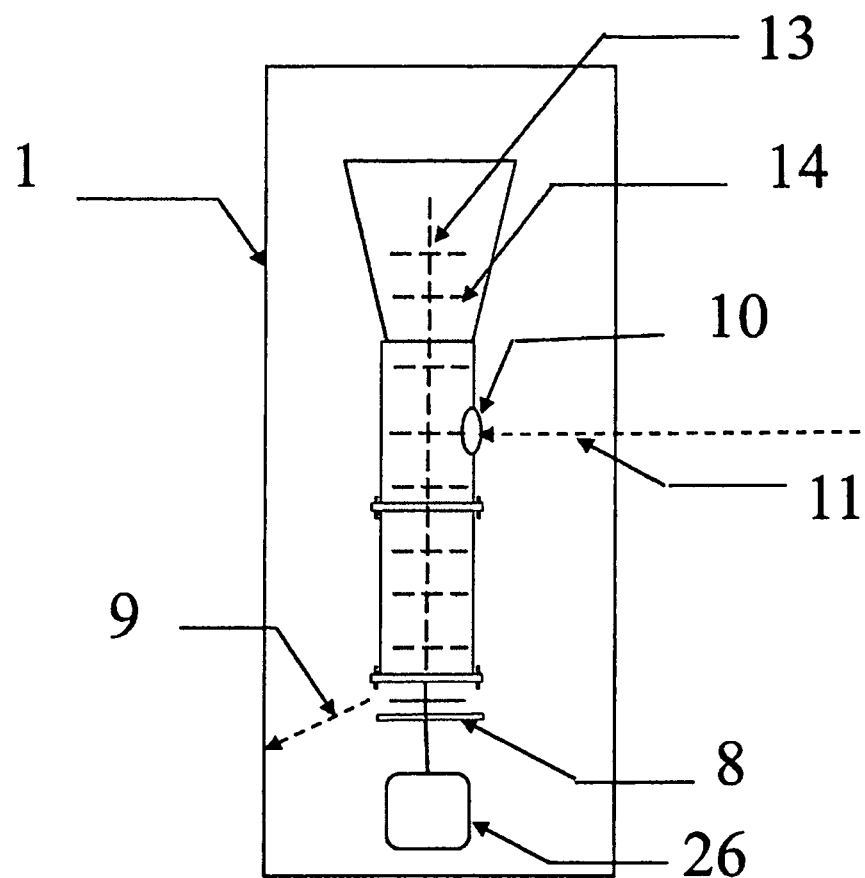
FIG. 2 provides a more detailed look at the internal components that make up the material flow system, depicted in FIG. 1. The material flow system provides the means to move the material through the SLT in a uniform manner, isolating the material from the laser-optics system.
Figure 3:
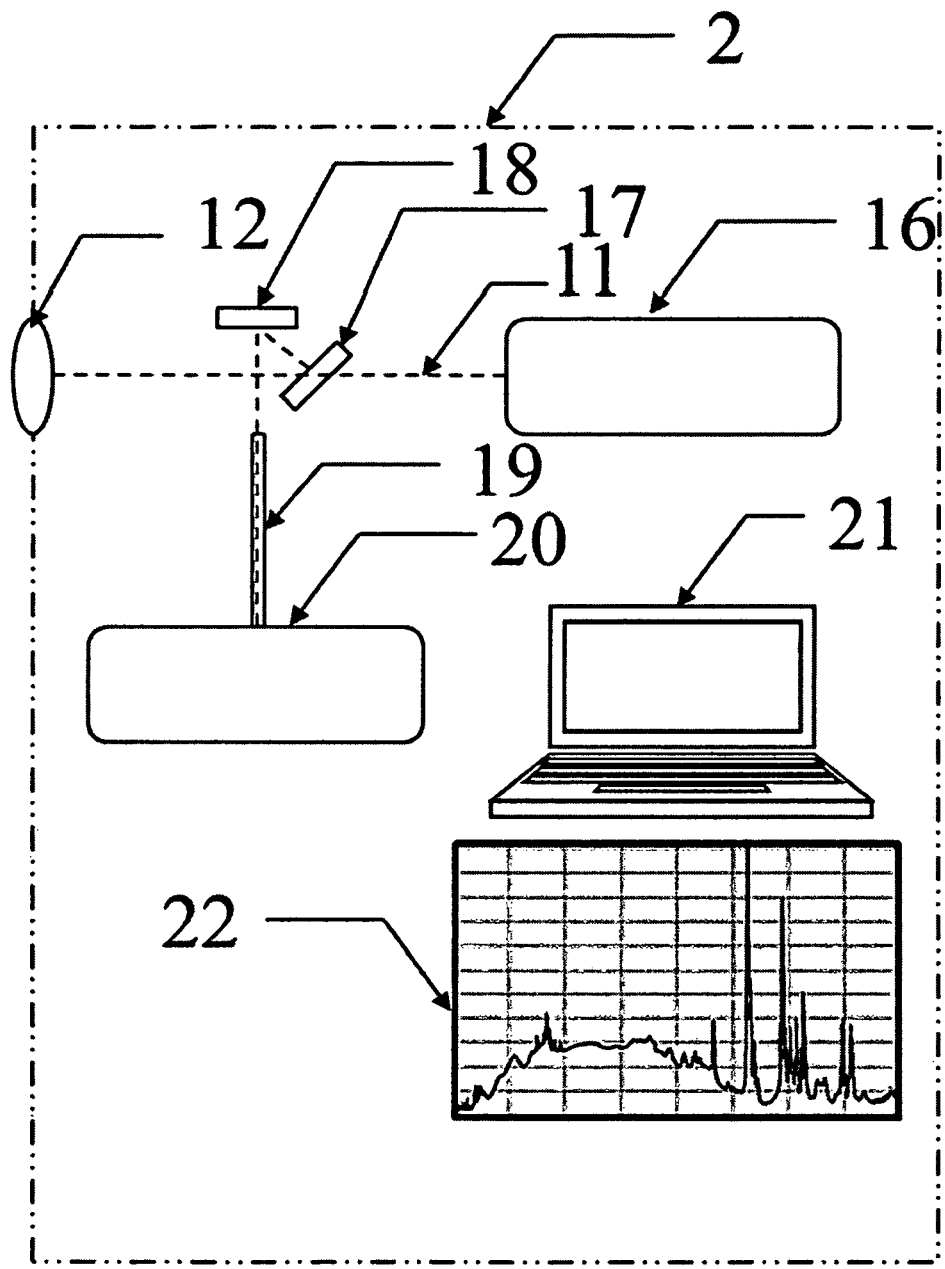
FIG. 3 provides a sectional view of one potential arrangement of optical components in the optical system depicted in FIG. 1, designed to transmit the laser light and receive the emission spectra inside the optical system chamber. This figure is a blown up view of the optical system referred to in FIG. 1.

Referring to the drawing, shown in FIG. 2, after entering into the Source Feed Hopper 5, the Source Target Materials 4 migrate down through the Material Flow Chute 6 until the Migrating Material 7 becomes Exiting Material 9 at the bottom of the chute. The Migrating Material 7 moves under the force of gravity, and the rotating and vertical motion of a Rotating Disk Rod 13, that is connected to Mixing Tools 14 attached to this rod at select vertical intervals, and the Flow Control Disk 8. While the Migrating Material 7 derives its downward motion from gravity, the presence of the Flow Control Disk 8 at the bottom of the Material Flow Chute 6 prevents a free flow of material through the system. As a result, the Migrating Material 7 is retained in a compacted column inside the Material Flow Chute 6. This compaction is important for laser targeting purposes, discussed in greater detail below.

To initiate flow through the SLT system, the Rotating Disk Rod 13 is lowered from its normally closed (up position) to provide clearance between the Flow Control Disk 8 and the bottom of the Material Flow Chute 6. This clearance provides space for the Exiting Material 9 to exit the bottom of the Material Flow Chute 6. To facilitate this flow and to prevent clogging of the Migrating Material 7, Mixing Tools 14 are attached to the Rotating Disk Rod 13. A Mixing Tool 14 can be a simple rod, perpendicular to the direction of material flow that rotates and mixes the sample material during its descent and prevents material binding in the Material Flow Chute 6. This latter point is very important if moist target materials, particularly fine grained materials, which are susceptible to binding, are introduced into the system.

The volumetric flow rate though the Material Flow Chute 6 is regulated by Flow Control Disk 8 clearance from the bottom of the Material Flow Chute 6 and the speed of rotation of the Rotating Disk Rod 13 and the Flow Control Disk 8. The faster the rotation the more rapid the material will move through the system. The rotating Flow Control Disk 8 imparts a centrifugal force to the Migrating Material 7 that has reached the Flow Control Disk 8, assisting in converting this Migrating Material 7 into Exiting Material 9.

The combined gravitational force on the Migrating Material 8 and the centrifugal force imparted by the Flow Control Disk 8 provides the means to move the material through the system. A Variable Speed Motor 26 can be conveniently used as part of the invention to provide different rotational speeds for the Flow Control Disk 8 and as a result different volumetric flow rates, depending on the particular needs of the user. For example more rapid rates will move more material through the SLT in a given time interval, but will provide shorter time intervals for laser targeting of the material. Slower flow rates will move less through the SLT in a given time interval, but will provide longer time intervals for laser targeting of the sample. The rate of flow of material through the system, expressed in terms of volume per time, for example gallons per minute (gpm), will depend on the particle size and the specific gravity the material. The smaller the particle size and the lower the specific gravity, the slower the flow rate for a given clearance or opening between the Flow Control Disk 8 and the bottom of the Material Flow Chute 6, and a given Flow Control Disk 8 rotational speed. Coarse stone with a nominal size of ½ inch was found to flow through the system at volumetric flow rates ranging from approximately 7 to 16 gpm. Fine wet sand was found to flow through the system at volumetric flow rates ranging from approximately 1 to 10 gpm, and fine powdered material, mortar mix, was found to flow through the system at volumetric flow rates ranging from 3 to 15 gpm. As will be discussed below such flow rates can be altered by additional operational requirements, for example material moisture reduction.

Determining the characteristics of the target material is dependent on exposure of the material to a high powered laser pulse of sufficient energy to ablate a small microgram-sized portion of the material so that light over a wide spectral range can be released as electrons interact and recombine with ions. Such high energy laser can be expected to be, for a Nd-YAG pulsed laser between 25 and 500 mJ. The Material Flow Chute 6 and the Flow Control Disk 8 provide the means to compact and control bulk material flow in a manner that provides for a uniform flow passed a Laser Targeting Orifice 10. The Laser Target Orifice 10 is a small hole, located in the side of the Material Flow Chute 6, strategically located to permit a Laser Beam 11 to pass through the Material Flow Chute 6 wall. Since the Migrating Material 7 fills the Material Flow Chute 6, due to the resistance provided by the Flow Control Disk 8, the solid particles are pressed tightly against the wall of the flow chute providing a nearly uniform focal distance from the laser outlet to the migrating material particles, minimizing focal length variability during SLT system operations. There will be some inevitable variability due to the heterogeneity in the particle shapes and sizes of the Source Target Materials 4. Such variability will be mitigated, if needed, by the use of chemometric modeling discussed previously or additionally by employing a laser to target autofocusing system, referenced further below.

Referring again to the drawing shown in FIG. 1, the Laser Beam 11 originates in the Laser-Optics System 2, where the laser and optical equipment described in detail, below is contained in a sealed housing. To exit the housing, the Laser Beam 11 passes through a Quartz Window 12 and subsequently passes through the Dust Suppression System 3, prior to reaching the Laser Targeting Orifice 10 and the Migrating Material 7.

Referring to FIG. 2, a blown up depiction of the Laser-Optics System 2, shows one of many potential arrangements for the laser-optics that would be used in such a system. Such an arrangement is familiar to those versed in the art of laser-optics technology and is shown here for completeness to teach how the laser-optics integrates into the Dust Suppression System 3 and the Material Flow System 1.

The Laser-Optics System 2 is enclosed in a sealed housing and contains the Laser 16, which generates a Laser Beam 11 that is directed through the Quartz Window 12. The Laser Beam 11, enroute to the Quartz Window 12, passes through a First Reflecting Mirror 17. Receiving light emission generated by the ablation process travels back through the Quartz Window 12, along the same line as the Laser Beam 11. This returning light emission is reflected off the First Reflecting Mirror 17 onto a Second Reflecting Mirror 18 that directs the returning light to a Waveguide 19, which can consist of a fiber optic cable for example, that transmits the returning light to a Spectrometer and Charge Coupled Detector 20. The Spectrometer and Charge Coupled Detector 20 transmits the electronic signals to a Computer 21 that can store the data for subsequent analysis and generate visually displayed Emission Spectra 22. To function with minimal interferences it is important for the Quartz Window 12, through which the Laser Beam 11 and the receiving spectra must pass, to be dust and dirt free. The inventors have incorporated a Dust Suppression System 3 into the SLT system to provide as one objective the maintenance of a clean Quartz Window 12.

Figure 4:
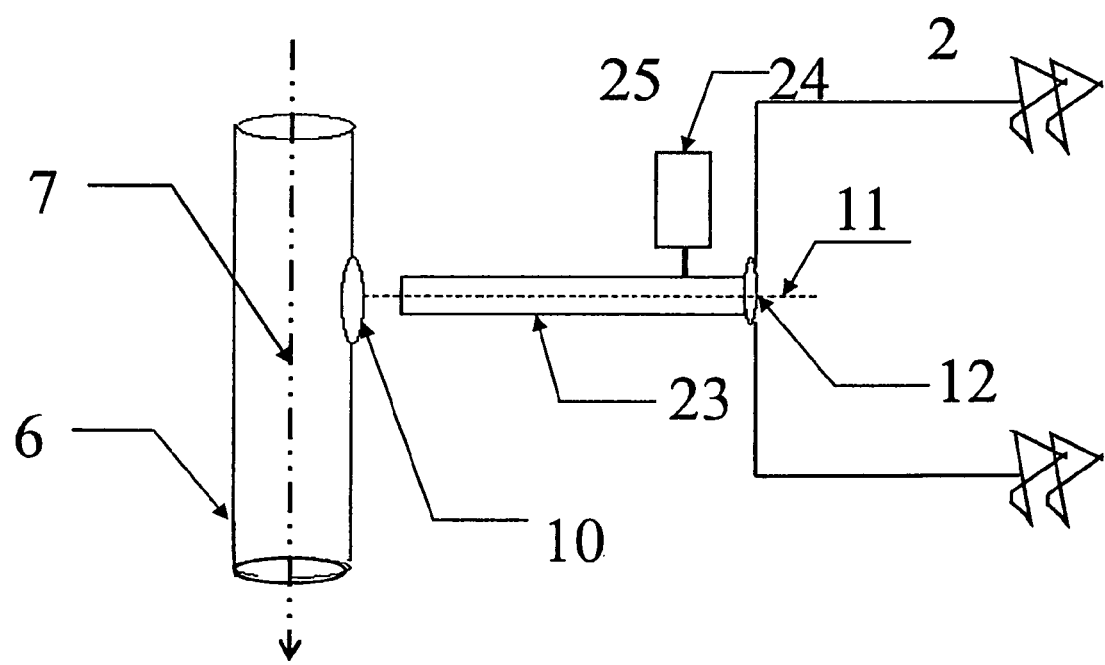
FIG. 4 provides a sectional, blown-up view of the dust suppression system, referred to in FIG. 1, which is situated between the laser and optical system housing and the target aperture.

Referring to FIG. 4, where a blown up view of the Dust Suppression System 3, is shown, the Laser Beam 11 exiting the Laser-Optic System 2 enters a Dust Suppression Tube 23. The Dust Suppression Tube 23 is a narrow, hollow tube with a small diameter, less than one-inch, sealed on the Laser-Optics System 2 side by the Quartz Window 12, and open on the side of the where the Laser Beam 12 exits the Dust Suppression Tube 23 and enters through the Laser Target Orifice 11 to couple with the Migrating Material 7.

During the laser ablation process, fine dust particles can be generated. The particles can eject from the Laser Target Orifice 10. It is also possible that additional dust could be generated during transport of the Migrating Material 7. Dust particles generated for any reason that are not removed from the system could interfere with the Laser Beam 11, and soil the Quartz Window 12. The dust particles could interfere with the energy reaching the target material. The Dust Suppression System 3 is incorporated into the SLT to minimize the significance of this problem. This is accomplished using pressurized air that can be supplied by an Air Compressor 24, or other suitable device, which provides the means to pressurize the Dust Suppression Tube 23. The introduction of compressed air into the Dust Suppression Tube 23 by the Air Compressor 24 results in pressurization of the Dust Suppression Tube 23 and directs air flow out of the tube at the Laser Target Orifice 10. This air flow has two purposes. It prevents dust from entering into the Dust Suppression Tube 23, thereby preventing contact of the dust with the Quartz Window 12, and it disperses dust generated during the ablation process preventing a buildup of dust particles in the vicinity of the Laser Target Orifice 10.

Additionally, by introducing an Air Heater and Blower 25, the temperature of the air inlet to the Dust Suppression Tube 23 can be elevated prior to it being directed at the Laser Target Orifice 10, or alternatively the hot air can be directed from the Air Heater and Blower 25 directly to the Target Orifice 10. Such hot air will be extremely useful for drying those materials passing the Laser Target Orifice 10 that have sufficiently high moisture content to interfere with the spectral image generated by the plasma. Since the Laser Target Orifice 10 is a small hole, less than 5 mm, for most materials, focusing the hot air stream at this point will result in rapid drying of the target location. While either of the above referenced approaches for heating air and directing the heated air at the target orifice can be employed, in fact the latter design may be preferable to minimize heat transfer from the preheated air to the components of the Dust Suppression Tube 23 to surrounding SLT components. If necessary, under conditions of high moisture content, the migration of material through the Material Flow Chute 6 can be paused to permit more thorough drying, in the event this becomes necessary. A predetermined timing sequence to coordinate a flow stop and flow start drying interval duration with laser operations can readily be achieved using a Computer or a Programmable Logic Controller (PLC).

If necessary, filtered air or selected gas can also be used as the inlet air stream to ensure that an absolute minimum of particulate matter enters the Dust Suppression Tube 23, if desirable, to control the atmosphere in the Dust Suppression Tube 23. Providing a mechanism for controlling the atmosphere in the Dust Suppression Tube 23, and at the Laser Target Orifice 10 could enhance the laser ablation process and the transmission of the generated emission. For purposes of this invention, the type of atmosphere is unimportant. What is important and novel is the means to control the atmosphere within the Dust Suppression System 3 configuration and the means to remove moisture from the specific location targeted by the laser, without having to dry the entire Source Target Material 4 sample.

As noted above, the removal of dust particle buildup in the vicinity of the Laser Target Orifice 10 is accomplished with the compressed air that exits from the Dust Suppression Tube 23. Blown with sufficient force the particles will be blown away from the Laser Target Orifice 10. Such a process can also be enhanced if needed by altering the frequency at which the laser fires, by introducing a delay of perhaps one or two seconds between firings to provide for a cleaning period sufficient to remove particles from the vicinity of the Laser Target Orifice 10.

Environmental control, particularly temperature and humidity will be required if the SLT is deployed in extreme temperature environments or if the temperature fluctuates on a continual basis. This is needed to maintain the operating stability of the laser, optics and spectrographic equipment. Employing adequate SLT system ventilation and a temperature control system inside the closed housing that contains the SLT system will be needed in such instances. Finally, auto-focusing of the laser to target focal length may be required in certain instances where extreme changes focal length changes in focal length causes severe aberrations in the spectral output data. This autofocus add-on can be provided without diminishing the overall objective and description of the invention.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended claims.

We claim:

1. A bulk sampling and laser-targeting system to provide for continuous or semicontinuous monitoring of a bulk stream of material comprising:
   a material flow system comprising a vertically extending flow chute for permitting gravitational flow of said material, said material comprising fine or coarse grained solid granular material including powder-like materials;
   a laser optics system for directing a pulsed laser beam into said material flowing through said flow chute through a target orifice in said flow chute for ablating a microgram-sized portion of said material so that a light emission over a wide spectral range is released as electrons interact and recombine with ions;
   a dust and moisture suppression system for preventing dust and moisture build-up from interfering with said laser beam traveling from said laser optics system to said flow chute; and
   means for delivering light emission from ablated material within said flow chute to a spectrometer for analyzing said light emission;
   said laser optics system delivering pulsed laser beams to said flowing material through a laser target orifice in said flow chute on a continuous or semi-continuous schedule, while said flow chute minimizes focal length variability of said flowing material including solid particles that are compacted in the flow chute and pressed tightly against a wall of said flow chute by the resistance provided by a flow control means that simultaneously facilitates flow and prevents clogging associated with said flow chute, thereby providing a nearly uniform focal distance from the laser outlet to the migrating material particles;

said means to facilitate flow and prevent clogging comprises a rotating disk rod and a mixing tool attached to said rotating disk rod, said mixing tool further having a normally closed, rotational flow control disk at an outlet of said flow chute for opening and rotating to permit flow, and to regulate flow through said flow chute.

2. The system of claim 1 in which said means for delivering light emission from said flow chute comprises an optical arrangement in said laser optics system having mirrors for deflecting light emission from said flow chute through a wave guide into said spectrometer, said optical system having a first reflecting mirror through which light from said laser passes and enters said flow chute, said first reflecting mirror deflecting said returning light emission to a second reflecting mirror for deflecting said light emission directly into said wave guide.

3. The system of claim 1 in which said dust and moisture suppression system comprises a tube having an entry quartz window from said laser optics system to said target orifice in said flow chute through which said laser beam and light emission from said flow chute passes.

4. The system of claim 3 having a compressor to pressurize said tube to prevent entry of any dust laden gas.

5. The system of claim 1 having a source feed hopper for delivering said material into an upper end of said flow chute.

6. The system of claim 1 having a variable speed motor to provide different rotational speeds of said flow control disk to provide different rotational speeds and volumetric flow rates.

7. The system of claim 3 wherein said dust suppression system further comprises an air heater and blower elevating the temperature of the air inlet to the said dust suppression tube prior to air being directed at said laser target orifice for drying said materials passing said laser target orifice that have sufficiently high moisture content to interfere with the spectral image generated by the plasma during said ablation process.

8. The system of claim 3 wherein said dust suppression system further comprises an air heater and blower, elevating the temperature of the air directly at said laser target orifice for drying said materials passing said laser target orifice that have sufficiently high moisture content to interfere with the spectral image generated by the plasma during said ablation process.

9. A method of bulk sampling and laser-targeting of a bulk stream of material comprising the steps of:

insert into a top opening of a vertically extending flow chute for gravitational flow through said flow chute of a material comprising fine or coarse grained solid granular material including powder-like materials;

directing a pulsed laser beam from a laser optics system into said material flowing through said flow chute through a target orifice in said flow chute for ablating a microgram-sized portion of said material so that light over a wide spectral range is released as electrons interact and recombine with ions;

using a dust and moisture suppression system for preventing dust and moisture build-up from interfering with said laser beam traveling from a laser optics system to said flow chute;

delivering light emission from said ablated material within said flow chute to a spectrometer for analyzing said light emission on a continuous or semi-continuous basis; and, delivering pulsed laser beams from said laser optics system to said flowing material through a laser target orifice in said flow chute on a continuous or semi-continuous schedule, while said flow chute minimizes focal length variability of said flowing material including solid particles that are compacted in the flow chute and pressed tightly against a wall of said flow chute by the resistance provided by a flow control means that simultaneously facilitates flow and prevents clogging associated with said flow chute, thereby providing a nearly uniform focal distance from the laser outlet to the migrating material particles;

wherein the step of facilitating flow and prevent clogging includes providing a rotating disk rod and a mixing tool attached to said rotating disk rod, said mixing tool further having a normally closed, rotational flow control disk at an outlet of said flow chute for opening and rotating to permit flow, and to regulate flow through said flow chute.

10. The method of claim 9 in which said step of delivering light emission from said flow chute comprises providing an optical arrangement associated with said laser beam having mirrors for deflecting light emission from said flow chute through a wave guide into said spectrometer, said optical arrangement having a first reflecting mirror through which light from said laser passes and enters said flow chute, said first reflecting mirror deflecting said returning light emission to a second reflecting mirror for deflecting said light emission directly into said wave guide.

11. The method of claim 9 in which use of said dust and moisture suppression system comprises providing a tube with an entry quartz window associated with said laser beam to said target orifice in said flow chute through which said laser beam and light emission from said flow chute passes.

12. The method of claim 11 further comprising the step of providing a compressor to pressurize said tube to prevent entry of any dust laden gas.

13. The method of claim 9 further comprising the step of providing a source feed hopper for delivering said material into an upper end of said flow chute.

14. The method of claim 1 further comprising the step of using a variable speed motor to provide different rotational speeds of said flow control disk to provide different rotational speeds and volumetric flow rates.

15. The method of claim 11 further comprising the steps of providing an air heater and blower elevating the temperature of the air inlet to the said dust suppression tube prior to air being directed at said laser target orifice and drying said materials passing said laser target orifice that have sufficiently high moisture content to interfere with the spectral image generated by the plasma during said ablation process.

16. The method of claim 11 further comprising the steps of providing an air heater and blower elevating the temperature of the air directly at said laser target orifice and drying said materials passing said laser target orifice that have sufficiently high moisture content to interfere with the spectral image generated by the plasma during said ablation process.

17. The method of claim 1 further comprising the step of generating spectral chemometric calibration models using principal components analysis and partial least squares reception analysis with materials that contain known properties, and comparing such models with spectral outputs of said light emission.

* * * * *